United States Patent [19]

Bott

[11] Patent Number: 5,175,364

[45] Date of Patent: * Dec. 29, 1992

[54] PREPARATION OF CARBONYL HALIDES

[75] Inventor: Kaspar Bott, Mannheim, Fed. Rep. of Germany

[73] Assignee: BASF Aktiengesellschaft, Ludwigshafen, Fed. Rep. of Germany

[*] Notice: The portion of the term of this patent subsequent to Aug. 20, 2008 has been disclaimed.

[21] Appl. No.: 707,840

[22] Filed: May 30, 1991

Related U.S. Application Data

[62] Division of Ser. No. 68,013, Jun. 29, 1987, Pat. No. 5,041,649.

[30] Foreign Application Priority Data

Jul. 11, 1986 [DE] Fed. Rep. of Germany ....... 3623422

[51] Int. Cl.$^5$ .............................................. C07C 51/62
[52] U.S. Cl. .................................................... 562/848
[58] Field of Search ......................................... 562/848

[56] References Cited

U.S. PATENT DOCUMENTS

| | | | |
|---|---|---|---|
| 2,378,048 | 6/1945 | Theobald | 562/848 |
| 2,411,982 | 12/1946 | Theobald | 562/848 |
| 2,517,898 | 8/1950 | Linville | 562/848 |
| 3,471,557 | 10/1969 | Coffield | 260/544 |
| 4,863,642 | 9/1989 | Blank | 562/848 |

Primary Examiner—Paul J. Killos
Attorney, Agent, or Firm—John H. Shurtleff

[57] ABSTRACT

Carbonyl halides I $$R^2-\underset{\underset{R^3}{|}}{\overset{\overset{R^1}{|}}{C}}-CO-X, \qquad I$$

where $R^1$ is H, alkyl, cycloalkyl, haloalkyl or halocycloalkyl, $R^2$ and $R^3$ are each alkyl, cycloalkyl, haloalkyl or halocycloalkyl and may furthermore be bonded to one another to form a 5-membered to 7-membered ring and X is halogen, are prepared by reacting an alkyl halide II $$R^2-\underset{\underset{R^3}{|}}{\overset{\overset{R^1}{|}}{C}}-X \qquad II$$

with carbon monoxide under superatmospheric pressure in the presence of a catalytic amount of a) aluminum bromide and in the presence or absence of a solvent or b) aluminum chloride or bromide and in the presence of a halohydrocarbon and a carbonyl halide of the formula III $$R^4-CH_2-CO-Hal \qquad III.$$

where $R^4$ is hydrogen or $C_1-C_4$-alkyl and Hal is halogen.

11 Claims, No Drawings

PREPARATION OF CARBONYL HALIDES

This application is a division of application Ser. No. 68,013, filed Jun. 29, 1987, now U.S. Pat. No. 5,041,649.

The present invention relates to an improved process for the preparation of carbonyl halides by reacting a secondary or tertiary alkyl halide with carbon monoxide under superatmospheric pressure in the presence of a catalytic amount of a Lewis acid and in the presence or absence of a solvent.

German Laid-Open Application DOS 3,128,445 discloses that secondary or tertiary alkyl halides can be reacted with carbon monoxide in the presence of aluminum chloride or iron chloride as a catalyst to give the corresponding acyl halides without equimolar amounts of catalysts being required. Good yields and selectivities are obtained in particular in the presence of aluminum chloride, so that the use of this catalyst appears to be essential to the success of this process, at all events when no other Bröstead or Lewis acids are used. The use of aluminum chloride is disadvantageous in that it is only poorly soluble in many solvent preferred for Friedel-Crafts syntheses, eg. methylene chloride, chloroform, tetrachloroethylene or trichlorobenzene. On the other hand, solvents in which aluminum chloride is readily soluble, such as nitrobenzene or sulfolane, deactivate the catalyst.

For a continuous reaction procedure, which is preferred in industry, it is important for a catalyst to be capable of being fed into the pressure reactor not in solid form but in solution, and of course its activity should not be reduced.

It is an object of the present invention to provide a catalyst which does not have the disadvantages described.

We have found that this object is achieved by a process for the preparation of carbonyl halides of the formula I

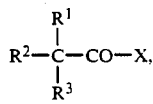    I where $R^1$ is hydrogen, alkyl, cycloalkyl, haloalkyl or halocycloalkyl, $R^2$ and $R^3$ are each alkyl, cycloalkyl, haloalkyl or halocycloalkyl and may furthermore be bonded to one another to form a 5-membered to 7-membered ring, and X is halogen, by reacting an alkyl halide of the formula II

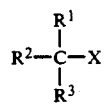    II with carbon monoxide under superatmospheric pressure in the presence of a catalytic amount of a Lewis acid, wherein the reaction is carried out in the presence of
a) aluminum bromide as a catalyst or
b) aluminum bromide or chloride as a catalyst and in the presence of a halohydrocarbon and a carbonyl halide of the formula III

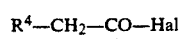    III where $R^4$ is hydrogen or $C_1$-$C_4$-alkyl and Hal is halogen.

The aluminum bromide, which is advantageously used in a concentration of from 0.005 to 0.05 mole per mole of alkyl halide II, is readily soluble in the solvents, such as halohydrocarbons, which are particularly suitable for the reactions. Examples of halohydrocarbons are bromohydrocarbons, preferably chlorohydrocarbons, in particular chloroalkanes, chloroalkenes, chlorocycloalkanes or chlorobenzene. Specific examples are methylene chloride, chloroform, tri- and tetrachloroethane, tetrachloroethylene, hexachlorobutadiene and mono-, di- and trichlorobenzene. Chloroalkanes and chloroalkenes, in particular those of 1 to 4 carbon atoms are particularly preferably used, methylene chloride and tetrachloroethylene being preferred. However, the reaction can also be carried out in the absence of a solvent if the alkyl halide II is liquid at the chosen reaction temperature.

The solubility of the aluminum bromide int he stated solvents, which in any case is good, can be further increased if carbonyl halides of the formula $R^4$—$CH_2$—CO—Hal, where $R^4$ is hydrogen or $C_1$-$C_4$-alkyl and Hal is halogen, in particular chlorine or bromine, are added as a solubilizing component. $C_2$- and $C_3$-acyl halides, eg. acetyl and propionyl chloride, are particularly suitable. The addition of these solubilizers also makes it possible to use aluminum chloride as a catalyst without solubility problems being encountered.

The amount of acyl halides can be about 0.1–2 moles per mole of aluminum halide. Preferably, from 0.1 to 1.5, in particular from 0.3 to 1.3, moles of acyl halide are used per mole of aluminum bromide, and from 0.5 to 1.8, in particular from 0.8 to 1.5, moles of acyl halide per mole of aluminum chloride.

The addition of the acyl halide does not result in any significant decrease in catalyst activity and no decarbonylation occurs, as may be the case, for example, when the products formed in the reaction are used as solubilizers.

Suitable starting materials II are alkyl halides in which the halogen atom X is, for example, fluorine, chlorine or bromine. It is advantageous to react alkyl bromides, and particularly advantageously to react alkyl chlorides. $R^1$ is hydrogen or branched or preferably straight-chain alkyl which is unsubstituted or substituted by one or more halogen atoms, such as fluorine or in particular chlorine bromine. Alkyl is, for example, of 1 to 20, preferably 1 to 10, in particular 1 to 5, carbon atoms. Specific examples of radicals $R^1$ are methyl, ethyl, propyl, isopropyl, butyl, isobutyl, amyl, isoamyl, hexyl, octyl and dodecyl, and specific examples of halogen-substituted alkyl radicals are chloromethyl, bromomethyl, fluoromethyl and ethyl, propyl, butyl, amyl, hexyl, heptyl, octyl, decyl or dodecyl, each of which is substituted by fluorine, chlorine or bromine.

$R^1$ may furthermore by cycloalkyl, preferably of 5 or 6 carbon atoms, which is unsubstituted or substituted by one or more of the abovementioned halogen atoms. Specific examples are cyclobutyl, cyclopentyl, cyclohexyl, methylcyclohexyl, chlorocyclopentyl, chlorocyclohexyl, bromocyclopentyl and bromocyclohexyl.

Apart from hydrogen, $R^2$ and $R^3$ have the meanings stated for $R^1$. Together with the carbon atom to which they are bonded, they may furthermore form a ring system which may also be bridged. In general, they are bonded to one another to form a 5-membered to 7-membered ring. Specific examples are the cyclopentyl, cyclohexyl, cycloheptyl, bicyclo[2,2,1]heptyl, bicyclo[2,2,2]octyl and bicyclo[3,2,1]octyl system. The started cycloalkyl radicals may furthermore be substituted by $C_1$-$C_4$-alkyl.

For example, the following starting materials may be used for the reaction: tert-butyl chloride and bromide, tert-amyl chloride and bromide, 1,2-dichloro-2-methylpropane, 2-chloro-2-methylhexane, 2-bromo-2-methylhexane, 2-chloro-2-propylhexane, 1-chloro-1-methylcyclohexane, norbornyl chloride and norbornyl bromide.

pressure was increased to 300 bar. The reaction mixture was then left to react for from 10 to 12 hours at the stated temperature, the CO pressure being kept constant at 300 bar.

Working up was carried out by adding an equimolar amount, based on the aluminum bromide, of dimethylformamide to the reaction mixture before the pressure is let down, and distilling off the reacted mixture from the catalyst under reduced pressure. The yields determined by gas chromatographic analysis of the distillate and details of the reaction are shown in the Table below.

TABLE $$RCl + CO \xrightarrow{AlBr_3} R-CO-Cl$$

| Example | RCl g/mol | AlBr$_3$ g/mol | Solvent g | Reaction at T = °C. | Yield$^{a)}$ g/% | Selectivity$^{a)}$ % |
|---|---|---|---|---|---|---|
| 1 | exo-norbornyl chloride 132/1.01 | 7/0.026 | — | 5–10 | 152/88$^{b)}$ | |
| 2 | tert-butyl chloride 600/6.48 | 20/0.075 | tetrachloroethylene 162 | 2–3 | 667/85.3 | 96.5 |
| 3 | tert-butyl chloride 600/6.48 | 30/0.11 | dichloromethane/ acetyl chloride 133/8.8 | 2–3 | 682/87.3 | 96.6 |

$^{a)}$based on starting materials RCl
$^{b)}$8.8 g of exo-norbornanecarbonyl bromide in addition = 4.3% yield$^{a)}$ The reaction is carried out batchwise or, preferably, continuously in a conventional manner under a carbon monoxide pressure of about 10–500, preferably 50–400, in particular 150–300, bar and at from $-20$ to $+80°$ C., preferably from 0° to 40° C., in particular from 0° to 10° C., the optimum reaction temperature depending to a great extent on the starting material II and the solvent used. The amount of solvent can be, for example, from 10 to 500, in particular from 20 to 100, advantageously from 20 to 50, % by volume, based on the volume of the alkyl halide used.

When the reaction is complete, the pressure can be let down to atmospheric pressure as in conventional processes, so that the product I formed, unconverted starting material II and any solvent present can be separated off from the catalyst. However, there is a danger that some of the carbonyl halide will be decomposed in a reaction which is the reverse of that in which it is formed. This decomposition can be substantially avoided if, before the pressure is let down, a carboxamide is added to the reaction mixture in order to destroy the Lewis acid catalyst. Acid amides of low molecular weight carboxylic acids, which can readily be separated from the reaction mixture, eg. amides of $C_1$-$C_5$-carboxylic acids, such as formic acid, acetic acid, propionic acid, butyric acid or valeric acid, are preferably used. A particularly preferred acid amide is dimethylformamide. To destroy the catalyst completely, equimolar amounts of the acid amide are added to the aluminum halide. Smaller or larger amounts are possible but are of no advantage.

Working up the reaction mixture by distillation is carried out in a conventional manner and therefore need not be described.

EXAMPLES 1 TO 3

The aluminum bromide, with or without the solvent or solubilizer, is initially taken in a stirred autoclave at $+5°$ C. Thereafter, carbon monoxide was forced in to give a pressure of 200 bar, the alkyl chloride was pumped in over from 30 to 80 minutes, and the CO

I claim:

1. In a process for the preparation of a carbonyl halide of the formula

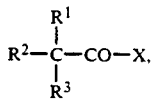   I wherein $R^1$ is hydrogen, alkyl, cycloalkyl, haloalkyl or halocycloalkyl, $R^2$ and $R^3$ are each alkyl, cycloalkyl, haloalkyl or halocycloalkyl and may furthermore be bonded to one another to form a 5-membered to 7-membered ring, and X is halogen, by reacting the corresponding halide of the formula

   II wherein $R^1$, $R^2$ and $R^3$ have the same meanings given above, with carbon monoxide under superatmospheric pressure in the presence of a catalytic amount of a Lewis acid, the improvement which comprises:
  carrying out the reaction in the presence of aluminum bromide as a catalyst in an amount of from 0.005 to 0.05 mole per mole of the halide reactant II and, optionally, adding a carboxamide when the reaction is complete to destroy said catalyst.

2. A process as claimed in claim 1, the halide reactant II is an alkyl chloride or bromide.

3. A process as claimed in claim 1, wherein the reaction is carried out under from 10 to 500 bar.

4. A process as claimed in claim 1, wherein the catalyst is destroyed when the reaction is complete by adding a carboxamide at the reaction pressure and then letting down the pressure for separation of the reaction products.

5. A process as claimed in claim 4 wherein the carboxamide is dimethyl formamide.

6. A process as claimed in claim 1, wherein the reaction temperature is from $-20°$ to $+80°$ C.

7. A process as claimed in claim 1, wherein the reaction pressure is from 50 to 400 bar and the reaction temperature is from 0° to 40° C.

8. A process as claimed in claim 1, wherein the reaction pressure is from 150 to 300 bar and the reaction temperature is from 0° to 10° C.

9. A process as claimed in claim 1, wherein the catalyst is destroyed when the reaction is complete by adding an amide of a $C_1$–$C_5$-carboxylic acid.

10. A process as claimed in claim 9, wherein the reaction is carried out at a pressure of about 150 to 300 bar, and at a temperature of about 0° to 10° C.

11. A process as claimed in claim 10, wherein the amide of the carboxylic acid is dimethyl formamide.

* * * * *

UNITED STATES PATENT AND TRADEMARK OFFICE
CERTIFICATE OF CORRECTION

PATENT NO. : 5,175,364
DATED : December 29, 1992
INVENTOR(S) : Kaspar Bott

It is certified that error appears in the above-identified patent and that said Letters Patent is hereby corrected as shown below:

IN THE CLAIMS:

Claim 2, line 1: after "claim 1," insert --wherein--.

Signed and Sealed this

Twenty-sixth Day of October, 1993

Attest:

BRUCE LEHMAN

Attesting Officer　　Commissioner of Patents and Trademarks